United States Patent [19]

Haight et al.

[11] Plant 5,213

[45] Apr. 3, 1984

[54] ROSE CV. CLIMBING OLE'

[75] Inventors: George S. Haight, San Jose; Herbert C. Swim, Ontario, both of Calif.

[73] Assignee: Armstrong Nurseries, Inc., Ontario, Calif.

[21] Appl. No.: 397,923

[22] Filed: Jul. 13, 1982

[51] Int. Cl.[3] ..... A01H 5/00

[52] U.S. Cl. ..... Plt./6

[58] Field of Search ..... Plt./6

*Primary Examiner*—Robert E. Bagwill

*Attorney, Agent, or Firm*—Synnestvedt & Lechner

[57] ABSTRACT

A climbing rose plant originating as a sport of Ole'.

1 Drawing Figure

1

This invention relates to a new variety of rose cv. Climbing Ole'. The plant is a climber and originated as a bud sport of the rose cv. "Ole'" (U.S. Plant Pat. No.2,474).

The sport was discovered by George Sievers Haight growing in a nursery in San Jose, Calif. and was first propagated by budding on Dr. Huey understock by Herbert C. Swim in Ontario, Calif. Subsequent reproduction of the plant by budding at both San Jose, Calif. and Ontario, Calif. have shown that the sport is stable in its essential characteristics and holds its distinguishing characteristics through succeeding propagations.

The characteristics of the sport are substantially identical to those of the parent Ole' as described in U.S. Plant Pat. No. 2,474 except as hereinafter noted.

The accompanying drawing is a black and white photograph of a 4 year old plant of the rose cv. Climbing Ole' growing outdoors in Ontario, Calif. that was taken in late February (early March) and shows the climbing habit of the sport.

2

The sport is a climber, whereas the parent rose Ole' is of a class falling midway between the hybrid tea and floribunda classes.

The sport has strong canes that obtain an overall length of about 8 to 10 feet, whereas the canes of the parent rose Ole' are of medium caliper and grow free in a bushy, upright-spreading and much-branched habit.

The parent rose cv. Ole' blooms nearly continuously on current season's wood during the growing season. In contrast, the sport flowers predominantly on second season's wood with a large flowering flush in spring followed by intermittent flowering during the remainder of the growing season.

We claim:

1. A new and distinct variety of rose as a sport of the rose cv. Ole' (U.S. Plant Pat. No. 2,474) characterized in that it is a climber and flowers on second season's wood, with a large flowering flush in the spring followed by intermittent flowering during the remainder of the growing season and otherwise having the characteristics of the parent rose cv. Ole'.

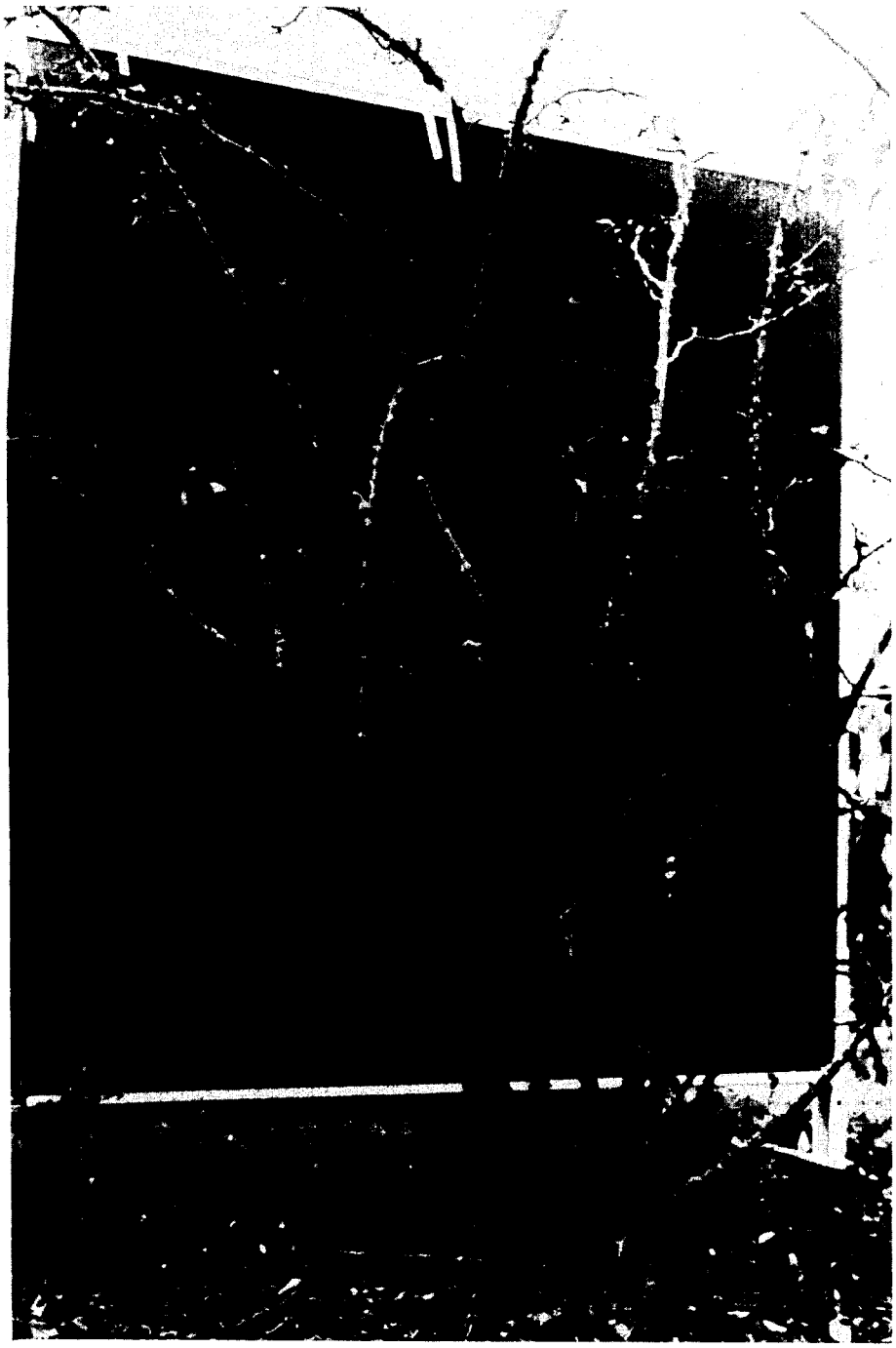

* * * * *